(12) United States Patent
Khan et al.

(10) Patent No.: US 12,420,074 B2
(45) Date of Patent: Sep. 23, 2025

(54) FLUID CONNECTOR ASSEMBLY

(71) Applicant: CAREFUSION 303, INC., San Diego, CA (US)

(72) Inventors: Mohammed Mehtab Khan, Bengaluru (IN); Seyed Alireza Salehi Borojerdi, Aliso Viejo, CA (US)

(73) Assignee: CAREFUSION 303, INC., San Diego, CA (US)

( * ) Notice: Subject to any disclaimer, the term of this patent is extended or adjusted under 35 U.S.C. 154(b) by 137 days.

(21) Appl. No.: 18/351,643

(22) Filed: Jul. 13, 2023

(65) Prior Publication Data

US 2025/0020256 A1   Jan. 16, 2025

(51) Int. Cl.
*A61M 39/10* (2006.01)
*A61M 39/26* (2006.01)

(52) U.S. Cl.
CPC ........ *A61M 39/10* (2013.01); *A61M 39/1011* (2013.01); *A61M 39/26* (2013.01); *A61M 2039/1027* (2013.01); *A61M 2039/1061* (2013.01); *A61M 2039/267* (2013.01)

(58) Field of Classification Search
CPC ...... A61M 39/1011; A61M 2039/1027; A61M 2039/1061; A61M 39/10; A61M 2039/267; A61M 39/26
See application file for complete search history.

(56) References Cited

U.S. PATENT DOCUMENTS

| 5,713,856 A | 2/1998 | Eggers et al. |
| 6,874,522 B2 | 4/2005 | Anderson et al. |
| 7,004,934 B2 | 2/2006 | Vaillancourt |
| 7,040,598 B2 | 5/2006 | Raybuck |
| 7,153,296 B2 | 12/2006 | Mitchell |
| 7,350,764 B2 | 4/2008 | Raybuck |
| 7,396,051 B2 | 7/2008 | Baldwin et al. |

(Continued)

FOREIGN PATENT DOCUMENTS

| EP | 1678070 A2 | 7/2006 |
| EP | 1517723 B1 | 1/2007 |

(Continued)

OTHER PUBLICATIONS

Bangert, Bill, "Shorter times to blood transfusion associated with decreased death risk in trauma patients", Medical Xpress, Apr. 14, 2016, https://medicalxpress.com/news/2016-04-shorter-blood-transfusion-decreased-death.html.

(Continued)

*Primary Examiner* — David Colon-Morales
(74) *Attorney, Agent, or Firm* — MASCHOFF BRENNAN

(57) ABSTRACT

Fluid connector assemblies that seal off fluid paths in the respective connectors are disclosed. When connectors of a fluid connector assembly are connected to each other, respective compressible members in the connectors are displaced, allowing downstream fluid passage through the fluid connector assembly. The fluid connector assemblies may further include a coupling mechanism for providing a connection between the connectors and maintain a connection that provides a threshold retention force. When an external force greater than the threshold force is applied to the fluid connector assembly, the connectors may be decoupled while the coupling mechanism may remain intact.

18 Claims, 7 Drawing Sheets

(56) References Cited

U.S. PATENT DOCUMENTS

| | | | |
|---|---|---|---|
| 7,731,244 B2 | 6/2010 | Miros et al. | |
| 7,763,013 B2 | 7/2010 | Baldwin et al. | |
| 7,766,394 B2 | 8/2010 | Sage et al. | |
| 7,794,675 B2 | 9/2010 | Lynn | |
| 7,803,139 B2 | 9/2010 | Fangrow, Jr. | |
| 7,803,140 B2 | 9/2010 | Fangrow, Jr. | |
| 7,815,614 B2 | 10/2010 | Fangrow, Jr. | |
| 7,918,243 B2 | 4/2011 | Diodati et al. | |
| 7,998,134 B2 | 8/2011 | Fangrow et al. | |
| 8,123,738 B2 | 2/2012 | Vaillancourt | |
| 8,142,418 B2 | 3/2012 | Mcmichael et al. | |
| 8,211,069 B2 | 7/2012 | Fangrow, Jr. | |
| 8,262,628 B2 | 9/2012 | Fangrow, Jr. | |
| 8,361,408 B2 | 1/2013 | Lynn | |
| 8,480,968 B2 | 7/2013 | Lynn | |
| 8,777,908 B2 | 7/2014 | Fangrow, Jr. | |
| 8,777,909 B2 | 7/2014 | Fangrow, Jr. | |
| 8,795,256 B1 * | 8/2014 | Smith | A61M 39/26 604/249 |
| 8,888,758 B2 | 11/2014 | Mansour | |
| 8,899,267 B2 | 12/2014 | Diodati et al. | |
| 8,910,919 B2 | 12/2014 | Bonnal et al. | |
| 8,974,425 B2 | 3/2015 | Tachizaki et al. | |
| 8,974,437 B2 * | 3/2015 | Williams | A61M 39/26 604/533 |
| 9,114,242 B2 | 8/2015 | Fangrow et al. | |
| 9,126,028 B2 | 9/2015 | Fangrow et al. | |
| 9,126,029 B2 | 9/2015 | Fangrow et al. | |
| 9,192,753 B2 | 11/2015 | Lopez et al. | |
| 9,234,616 B2 | 1/2016 | Carrez et al. | |
| 9,358,379 B2 | 6/2016 | Fangrow, Jr. | |
| 9,433,769 B2 | 9/2016 | Bayly | |
| 9,468,749 B2 | 10/2016 | Mansour et al. | |
| 9,492,649 B2 | 11/2016 | Carrez et al. | |
| 9,636,492 B2 | 5/2017 | Fangrow, Jr. | |
| 9,724,504 B2 | 8/2017 | Fangrow, Jr. et al. | |
| 9,724,505 B2 | 8/2017 | Williams et al. | |
| 9,861,805 B2 | 1/2018 | Dennis et al. | |
| 9,933,094 B2 * | 4/2018 | Fangrow | A61M 39/1011 |
| 9,974,939 B2 | 5/2018 | Fangrow, Jr. | |
| 9,974,940 B2 | 5/2018 | Fangrow, Jr. | |
| 10,029,086 B2 | 7/2018 | Nowak et al. | |
| 10,156,306 B2 | 12/2018 | Fangrow | |
| 10,173,045 B2 | 1/2019 | Mansour | |
| 10,179,203 B1 | 1/2019 | Huslage et al. | |
| 10,315,025 B2 * | 6/2019 | Phillips | A61M 39/26 |
| 10,398,887 B2 | 9/2019 | Fangrow, Jr. et al. | |
| 10,441,507 B2 | 10/2019 | Sanders | |
| 10,518,078 B2 | 12/2019 | Stjernberg Bejhed et al. | |
| 10,569,073 B2 * | 2/2020 | Hallisey | A61M 39/26 |
| 10,625,068 B2 | 4/2020 | Leuthardt et al. | |
| 10,655,768 B2 * | 5/2020 | Jones | A61M 39/24 |
| 10,697,570 B2 | 6/2020 | Fangrow | |
| 10,744,315 B2 | 8/2020 | Sanders | |
| 10,842,982 B2 | 11/2020 | Fangrow, Jr. | |
| 10,857,346 B2 | 12/2020 | Dennis et al. | |
| 10,864,362 B2 * | 12/2020 | Jones | A61M 39/1011 |
| 10,881,847 B2 | 1/2021 | Lynn | |
| 11,168,818 B2 | 11/2021 | Fangrow | |
| 11,207,514 B2 | 12/2021 | Kakinoki | |
| 11,235,135 B2 | 2/2022 | Tsai | |
| 11,273,297 B2 | 3/2022 | Kakinoki | |
| 11,484,471 B2 | 11/2022 | Sanders | |
| 11,491,084 B2 | 11/2022 | Ueda et al. | |
| 11,708,924 B2 * | 7/2023 | Mansour | F16L 37/0985 251/149 |
| 12,023,462 B2 * | 7/2024 | Kumar | F16L 37/30 |
| 12,109,387 B2 * | 10/2024 | Feith | F16L 55/1015 |
| 2004/0215158 A1 | 10/2004 | Anderson | |
| 2005/0090805 A1 | 4/2005 | Shaw et al. | |
| 2006/0129109 A1 * | 6/2006 | Shaw | A61M 39/26 604/246 |
| 2007/0088292 A1 | 4/2007 | Fangrow | |
| 2007/0088293 A1 | 4/2007 | Fangrow | |
| 2007/0088294 A1 | 4/2007 | Fangrow | |
| 2007/0225635 A1 | 9/2007 | Lynn | |
| 2008/0039803 A1 | 2/2008 | Lynn | |
| 2011/0106046 A1 | 5/2011 | Hiranuma | |
| 2011/0204621 A1 | 8/2011 | Whitaker et al. | |
| 2014/0249487 A1 | 9/2014 | Lynn | |
| 2014/0330254 A1 | 11/2014 | Rosenberger et al. | |
| 2016/0000363 A1 | 1/2016 | Jones et al. | |
| 2018/0200147 A1 | 7/2018 | Sanders | |
| 2019/0184152 A1 | 6/2019 | Kakinoki | |
| 2019/0282797 A1 | 9/2019 | Tsai | |
| 2020/0113784 A1 | 4/2020 | Lopez et al. | |
| 2020/0179672 A1 | 6/2020 | Kakinoki | |
| 2020/0215319 A1 | 7/2020 | Fangrow, Jr. et al. | |
| 2020/0284385 A1 | 9/2020 | Fangrow | |
| 2020/0323734 A1 | 10/2020 | Ueda et al. | |
| 2020/0338331 A1 | 10/2020 | Sanders | |
| 2021/0069484 A1 | 3/2021 | Tsa | |
| 2021/0077803 A1 | 3/2021 | Lynn | |
| 2021/0252267 A1 | 8/2021 | Fangrow, Jr. | |
| 2021/0268255 A1 | 9/2021 | O'Neil | |
| 2021/0388926 A1 | 12/2021 | Martin et al. | |
| 2021/0393938 A1 | 12/2021 | Lynn et al. | |
| 2021/0404587 A1 * | 12/2021 | Mansour | F16L 37/091 |
| 2022/0260189 A1 * | 8/2022 | Deuse | C12M 37/04 |
| 2022/0282814 A1 | 9/2022 | Fangrow | |
| 2023/0149689 A1 * | 5/2023 | Armstrong | A61M 39/26 604/93.01 |
| 2023/0310824 A1 * | 10/2023 | Shauver | A61M 39/22 604/500 |

FOREIGN PATENT DOCUMENTS

| | | | |
|---|---|---|---|
| EP | 1622675 B1 | 8/2009 | |
| EP | 2144634 A1 | 1/2010 | |
| EP | 2298407 A1 | 3/2011 | |
| EP | 2694132 A1 | 2/2014 | |
| EP | 2562456 B1 | 6/2014 | |
| EP | 2782633 A1 | 10/2014 | |
| EP | 1842002 B1 | 4/2015 | |
| EP | 2736582 B1 | 5/2015 | |
| EP | 2089094 B1 | 1/2016 | |
| EP | 2219721 B1 | 12/2017 | |
| EP | 2753396 B1 | 12/2017 | |
| EP | 2736584 B1 | 4/2018 | |
| EP | 3305361 A1 | 4/2018 | |
| EP | 2271398 B1 | 11/2018 | |
| EP | 2480281 B1 | 11/2018 | |
| EP | 2790750 B1 | 11/2018 | |
| EP | 2331191 B1 | 3/2019 | |
| EP | 3079756 B1 | 3/2019 | |
| EP | 2121114 B1 | 5/2019 | |
| EP | 2719419 B1 | 5/2019 | |
| EP | 2956204 B1 | 8/2019 | |
| EP | 3421077 B1 | 8/2019 | |
| EP | 3530313 A1 | 8/2019 | |
| EP | 3538201 A1 | 9/2019 | |
| EP | 3570807 A1 | 11/2019 | |
| EP | 3570809 A1 | 11/2019 | |
| EP | 2536463 B1 | 4/2020 | |
| EP | 3381505 B1 | 5/2020 | |
| EP | 3538201 B1 | 5/2020 | |
| EP | 1904152 B1 | 12/2020 | |
| EP | 2150307 B1 | 12/2020 | |
| EP | 3313490 B1 | 1/2021 | |
| EP | 3760275 A1 | 1/2021 | |
| EP | 3851155 A1 | 7/2021 | |
| EP | 3517164 B1 | 9/2021 | |
| EP | 3954355 A1 | 2/2022 | |
| EP | 3960229 A1 | 3/2022 | |
| EP | 3973044 A1 | 3/2022 | |
| EP | 3305361 B1 | 5/2022 | |
| EP | 3134052 B1 | 8/2022 | |
| EP | 3530313 B1 | 8/2022 | |
| WO | WO-2021099437 A1 | 5/2021 | |
| WO | WO-2021180675 A1 | 9/2021 | |
| WO | WO-2021252197 A1 | 12/2021 | |
| WO | WO-2022042956 A1 | 3/2022 | |

(56) References Cited

FOREIGN PATENT DOCUMENTS

| WO | WO-2022149339 A1 * | 7/2022 | ............ A61M 39/10 |
|---|---|---|---|
| WO | WO-2022207560 A1 | 10/2022 | |

OTHER PUBLICATIONS

Icumedical, "ChemoClave™ Needlefree Close System Transfer Device (CSTD)", date unknown, https://www.icumed.com/products/oncology/closed-system-transfer-devices/chemoclave.

Icumedical, "ChemoLock™ Needlefree Closed System Transfer Device (CSTD)", date unknown, https://www.icumed.com/products/oncology/closed-system-transfer-devices/chemolock.

Ivteam, "Force-activated separation IV connectors", 2022, Retrieved from the internet https://www.ivteam.com/intravenous-literature/force-activated-separation-iv-connectors/ [Last retrieved Jan. 13, 2023].

Lineus Medical, SafeBreak Product Features and Benefits Brochure, May 2021, mkg 0058 May 2021 Rev. 02.

Przen, "Lineus Medical Goes International, Signs ONEY for Distribution in Korea", PRZen Online Press Release Distribution, PrZen/33448014, MKG-0130 Rev 00, Retrieved from the internet https://przen.com/pr/lineus-medical-goes-international-signs-oney-for-distribution-in-korea-przen-33448014 [Last retrieved Jan. 13, 2023].

Rickard, et al., "Securing All intraVenous devices Effectively in hospitalised patients—the SAVE trial: study protocol for a multicentre randomised controlled trial", BMJ Open, Sep. 23, 2015;5(9):e008689, doi: 10.1136/bmjopen-2015-008689. PMID: 26399574; PMCID: PMC4593168.

TADA Group AB, LinkedIn Post "ReLink granted patent in Japan", LinkedIn, Mar. 2022, retrieved from the internet https://se.linkedin.com/company/tadamedical?trk=public_post_reshare_feed-actor-image&original_referer= [Last retrieved Mar. 2022].

Tribology, "Coefficient of friction, Rolling resistance and Aerodynamics", date unknown, https://www.tribology-abc.com/abc/cof.htm.

International Search Report and Written Opinion for Application No. PCT/US2024/037208, dated Oct. 2, 2024, 11 pages.

* cited by examiner

FLUID CONNECTOR ASSEMBLY

TECHNICAL FIELD

The present disclosure relates generally to medical fluid connectors and, more particularly, to a fluid connector assembly that includes medical connectors that decouple with each other due to an applied force, with each medical connector designed to automatically seal off their respective fluid paths. The decoupling may be due to intentional or unintentional separation between the medical connectors.

BACKGROUND

Peripheral intravenous ("PIVC") catheters are medical tools inserted into peripheral veins of patients to deliver medical fluid to the patients. In an example application, the medical fluid is delivered to the patient, and a medical professional subsequently removes the PIVC catheter from the patient. Often, however, these catheters are unintentionally dislodged. For example, catheter lines receiving an unintended or unexpected pulling force can pull the IV tubing, which pulls the catheter out of the patient. In other instances, catheters are accidentally removed from patients and medical professionals. Unintended or unexpected dislodgement can lead to patient blood loss, IV fluid loss, and IV fluid delivery delay.

SUMMARY

In accordance with at least some embodiments disclosed herein is the realization that unintended dislodgement or disconnection of a medical connection, such as a medical fluid line, can result in injury to a patient or a medical professional, such as by depriving the patient of a medicament, increasing the potential for infection to the patient, and exposing the medical professional to medicaments.

Aspects of the present disclosure provide fluid connector assemblies with medical connectors, each of which include one or more fluid paths, that respond to unintentional or unexpected external forces by decoupling from each other and sealing off their respective fluid paths. The decoupling may include automatic decoupling using bellows or other elastically compressible member that decompress and return to their original shape external forces are no longer acting upon them. Beneficially, fluid connector assemblies described herein can limit or prevent patient blood loss, IV fluid loss, infection, and medical delivery delays. Further, aspects of the present disclosure provide connecting mechanisms that aid in the connection of the fluid connector assembly in the event that the fluid connector assembly is decoupled.

BRIEF DESCRIPTION OF THE DRAWINGS

Various features of illustrative embodiments of the inventions are described below with reference to the drawings. The illustrated embodiments are intended to illustrate, but not to limit, the inventions. The drawings contain the following figures.

DETAILED DESCRIPTION

Figure 1:
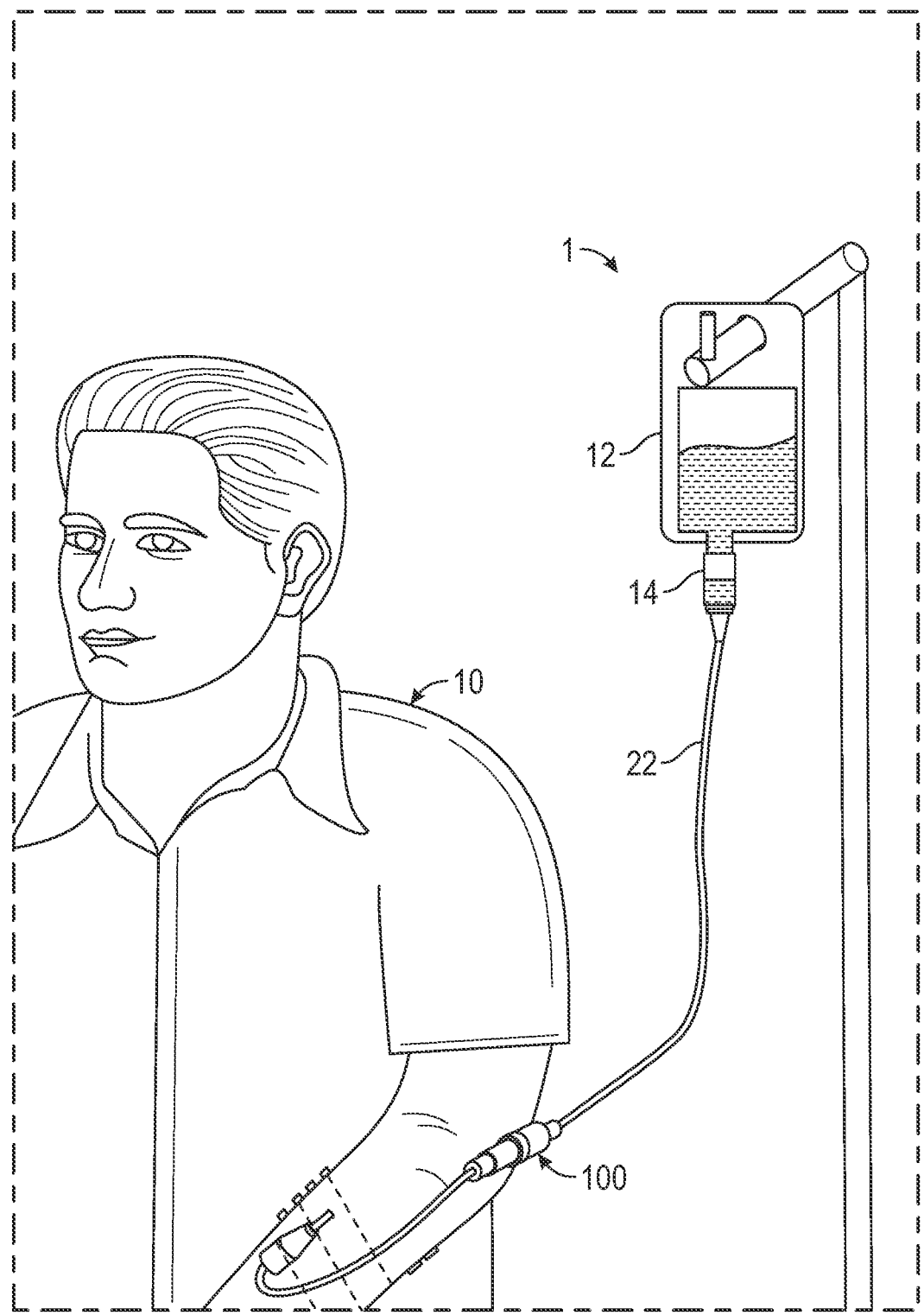
FIG. 1 illustrates an IV set coupled to a patient, in accordance with aspects of the present disclosure.

In the following detailed description, numerous specific details are set forth to provide a full understanding of the subject technology. It should be understood that the subject technology may be practiced without some of these specific details. In other instances, well-known structures and techniques have not been shown in detail so as not to obscure the subject technology.

Further, while the present description sets forth specific details of various embodiments, it will be appreciated that the description is illustrative only and should not be construed in any way as limiting. Additionally, it is contemplated that although particular embodiments of the present disclosure may be disclosed or shown in the context of an IV set, such embodiments can be used in other fluid conveyance systems. Furthermore, various applications of such embodiments and modifications thereto, which may occur to those who are skilled in the art, are also encompassed by the general concepts described herein.

The disclosed coupler assembly overcomes several challenges discovered with respect to certain IV catheters. When a higher full force is exerted upon the catheter than the securement method was designed to withstand, it may result in catheter dislodgement. In such cases, a nurse may need to change the catheter, which causes pain to the patient and requires additional costs and time be invested by the nurse for new catheterization. Examples of such catheter dislodgement scenarios include a patient rolling over in bed or catching their IV lines on bed rails, transfers of patients to different beds, fidgeting by pediatric patients, visitors catching on the lines, and/or disoriented adult patients pulling out their lines. Because the accidental or unintentional dislodgement of tubing, catheters, or fittings may interrupt the administration of medical fluids and may cause discomfort to patients, the use of certain conventional IV lines is undesirable.

Therefore, in accordance with the present disclosure, it is advantageous to provide couplers and coupler/connector assemblies as described herein that allow for the disconnection of an IV line at the point of the coupler assembly. This disconnection point may help avoid catheter dislodgement and may provide an easy point of re-connection that is additionally easy to clean.

In accordance with some embodiments, the present disclosure includes various features and advantages of a fluid connector assembly with medical connectors that seal off their respective fluid paths when the medical connectors are decoupled from each other. The medical connectors may each include a compressible member that decompresses in response to the decoupling, thus providing an automatic sealing of the respective fluid paths. The fluid connector assembly may further include a coupling mechanism that couples to the fluid connector assembly that allows for non-permanent connection that preventing over straining as well as limits an interstitial gap opening to minimize microbial growth.

Referring now to the figures, FIG. 1 illustrates an IV set 1 coupled to a patient 10, in accordance with aspects of the present disclosure. The IV set 1 includes a medicament bag 12, a drip chamber 14, and tubing 22. The tubing 22 extends between the drip chamber 14 and a fluid connector assembly 100 of the IV set 1. To resist unintended dislodgement or disconnection of the tubing 16 or the catheter 18 from the patient, tape is placed over the tubing 16 and the catheter, so that the tape engages the tubing 22, the catheter, and the patient 10.

Figure 2:
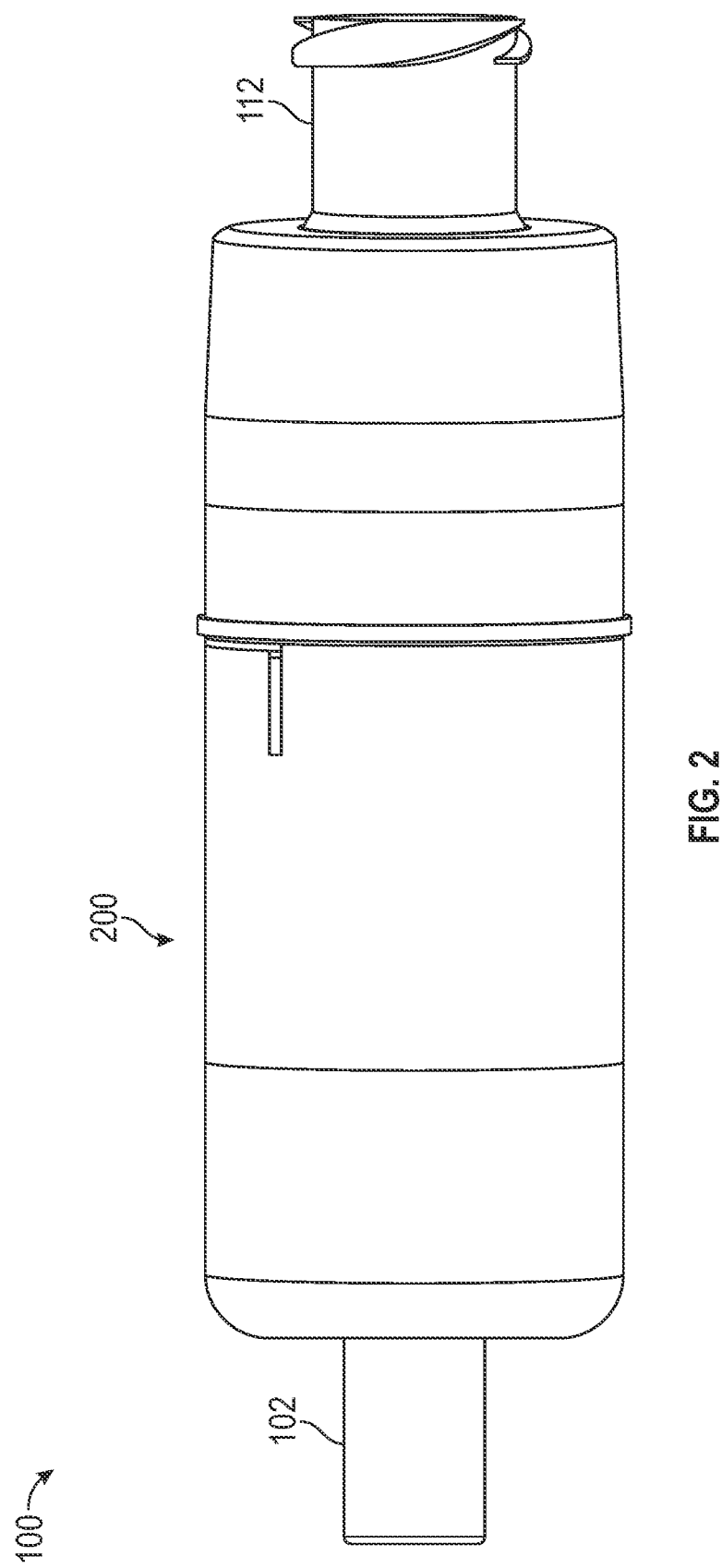
FIG. 2 illustrates a side view of the fluid connector assembly as assembled, in accordance with aspects of the present disclosure.

FIG. 2 illustrates a side view of a fluid connector assembly 100, in accordance with aspects of the present disclosure. The fluid connector assembly 100 is designed for use in medical applications, such as the IV set 1 (shown in FIG. 1) as well as other IV medical fluid delivery applications using catheters, including PIVC catheters, as non-limiting examples.

As shown, the fluid connector assembly 100 may include a connector 102 and a connector 112 coupled with the connector 102 and a coupling mechanism 200. The connector 102 and the connector 112 may be referred to as a first connector and a second connector, respectively. However, "first" and "second" may be interchangeable. Also, each of the connectors 102 and 112 may be referred to as medical connectors. When the connectors 102 and 112 are connected to each other as shown in FIG. 2, a fluid path for medical fluid is established by the fluid connector assembly 100.

In some embodiments, the connector 112 is connected to a medical fluid (not shown). Further, in some embodiments, the connector 102 is connected to a catheter line (not shown) that delivers the medical fluid to a catheter.

Figure 3:
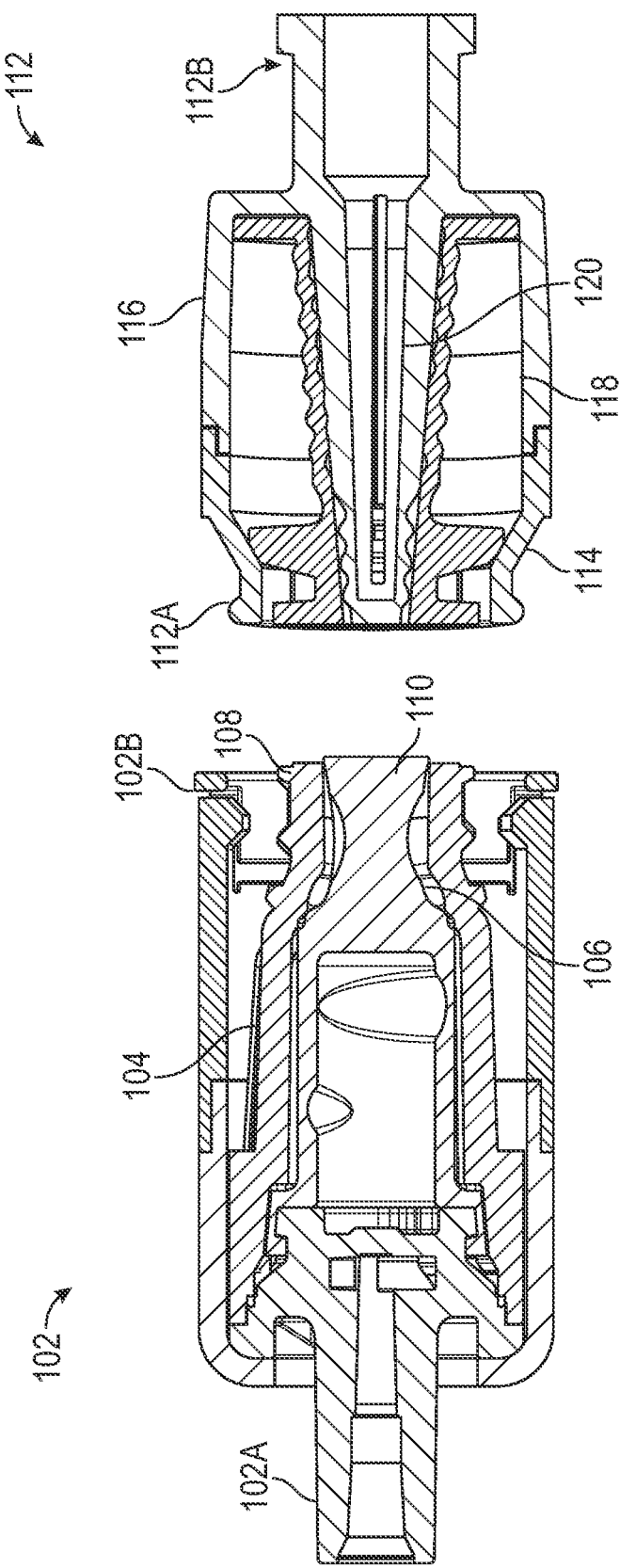
FIG. 3 illustrates a cross-sectional view of the connectors of the fluid connector assembly, in accordance with aspects of the present disclosure.

Referring to FIG. 3, the connector 102 may include a first end 102A and a second end 102B opposite the first end 102A. The connector 102 may include an exterior surface 104 and an interior surface 106. The exterior surface 104 may include a one or more threads 108 positioned at the second end 102B of the connector 102. The connector 102 may include a hollow, or generally hollow, body that carries one or more components. For example, a compressible member 110, may be housed within the connector 102.

In some embodiments, the compressible member 110 includes a resilient valve member or bellow that can elastically compress. Accordingly, the compressible member 110 can compress by an external force and subsequently return to its original, uncompressed form when the external force is removed. The compressible member 110 may be designed to regulate fluid flow through the connector 102.

Similar to the connector 102, the connector 112 may include a first end 112A and a second end 112B opposite the first end 112A. The connector 112 may further include a forward portion 114. In some embodiments, the forward portion 114 may be formed separately from the connector 112 and coupled proximate the first end 112A by any suitable connecting means. In other embodiments, the forward portion 114 may be integrally formed with the connector 112 as a unitary structure. The connector 112 may include an exterior surface 116 and an interior surface 118. The connector 112 may include a hollow, or generally hollow, body that carries one or more components. For example, the connector 112, may include valve member 120. The valve member 120 may be configured to contact the compressible member 110 when the connectors 102, 112 are coupled.

Figure 5:
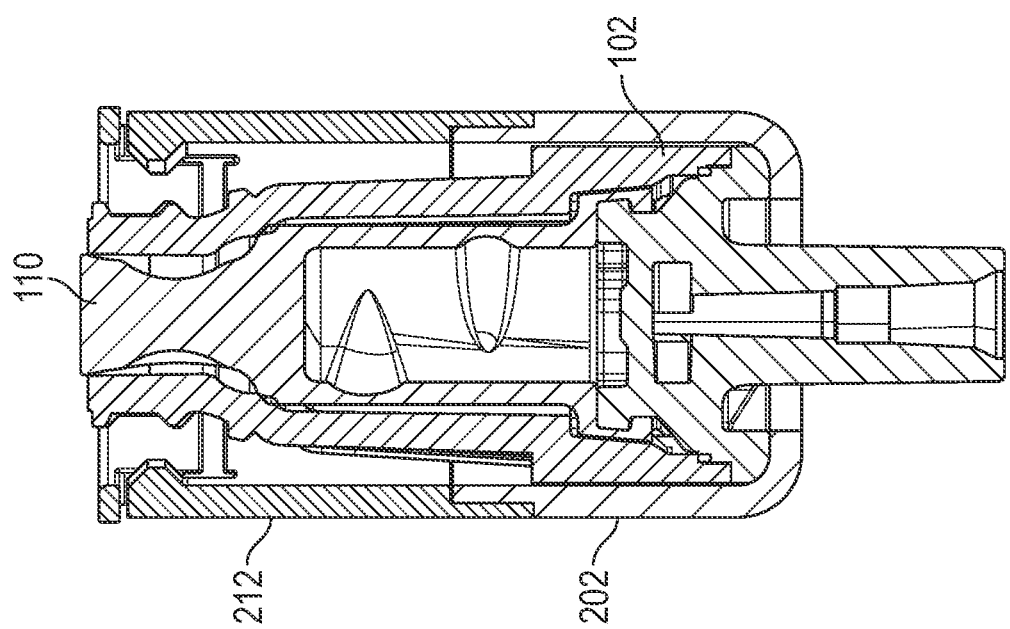
FIG. 5 illustrates a cross-sectional view of the coupling mechanism of the fluid connector assembly, in accordance with aspects of the present disclosure.
Figure 4:
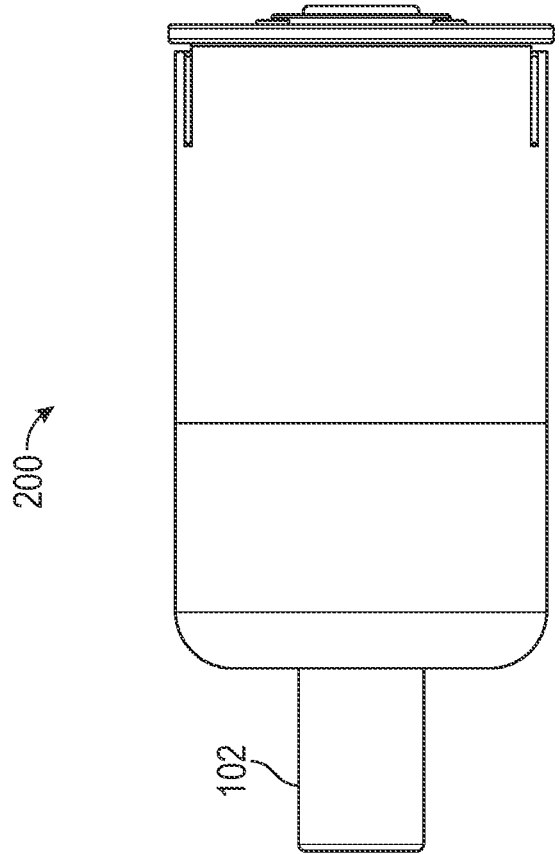
FIG. 4 illustrates a side view of a coupling mechanism of the fluid connector assembly, in accordance with aspects of the present disclosure.

Referring to FIGS. 4-5, the fluid connector assembly 100 may further include a coupling mechanism 200 that couples to the connectors 102, 112. The coupling mechanism 200 may include a first member 202, also referred to as an anchor cap, and a second member 212, also referred to as a snap cap. In some embodiments, the coupling mechanism 200 is manufactured through injection molding and formed of polycarbonate, however the coupling mechanism 200 need not be so limited. For example, the coupling mechanism may be formed of any suitable material, including but not limited to, polypropylene, polyethylene, acrylics.

Figure 7A:
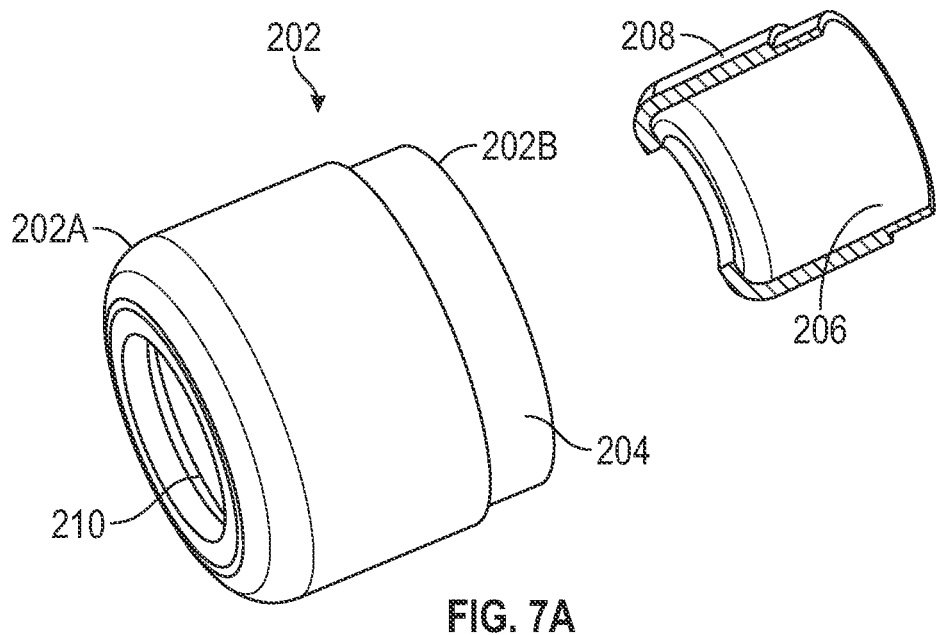
FIGS. 7A-7B illustrate views of a coupling mechanism of the fluid connector assembly, in accordance with aspects of the present disclosure.
Figure 7B:
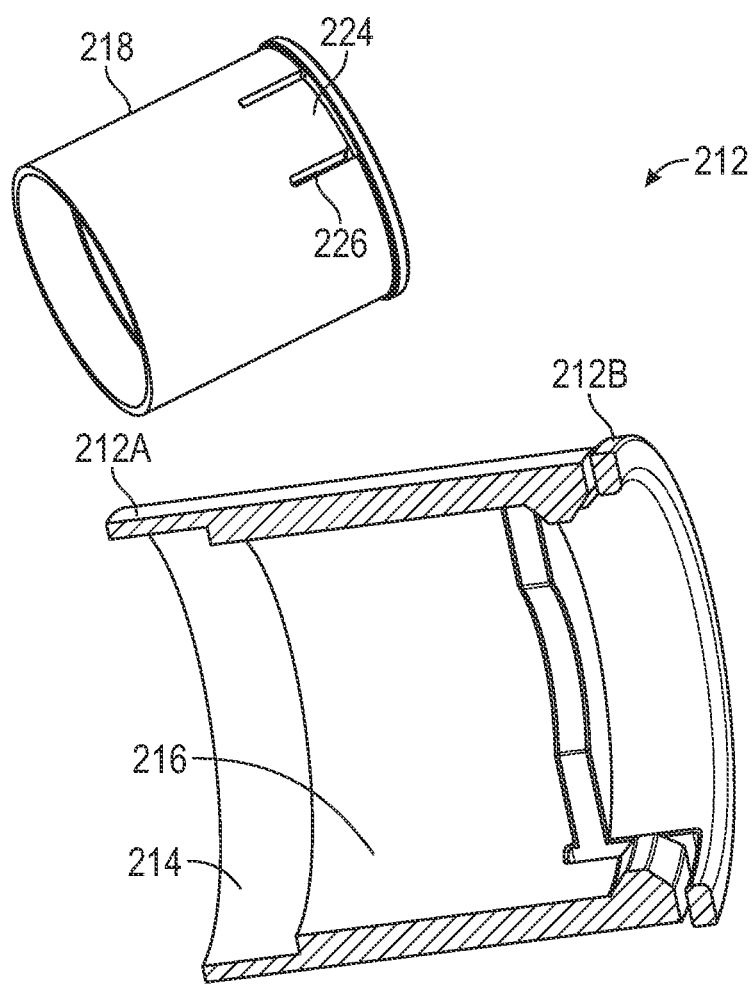
Figure 8:
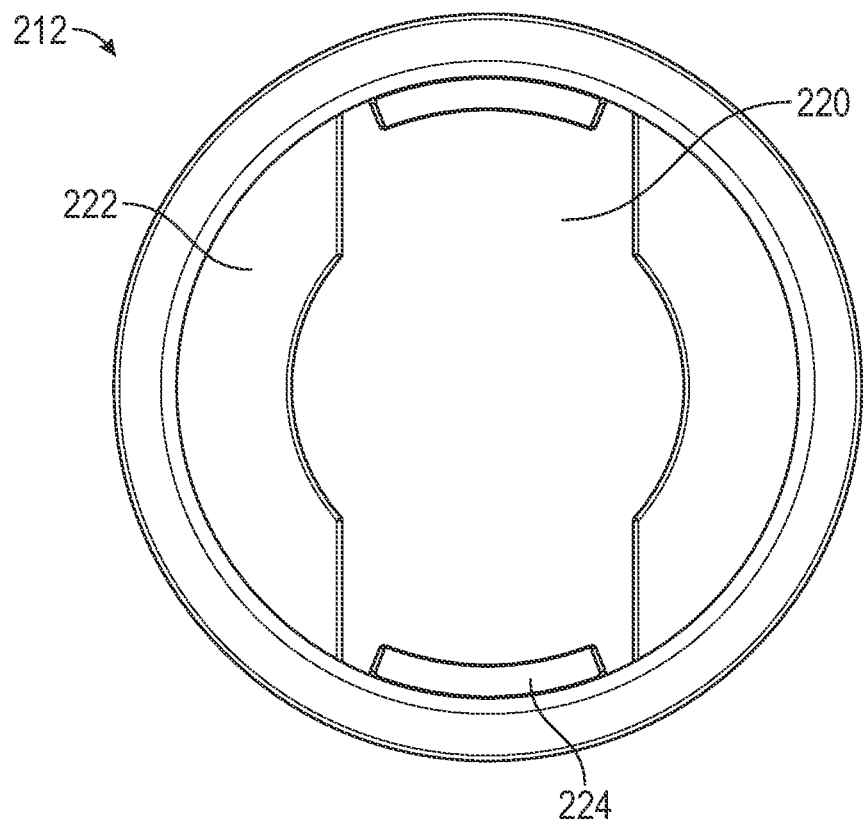
FIG. 8 illustrates a partial cross-sectional view of a coupling mechanism of the fluid connector assembly, in accordance with aspects of the present disclosure.
Figure 9:
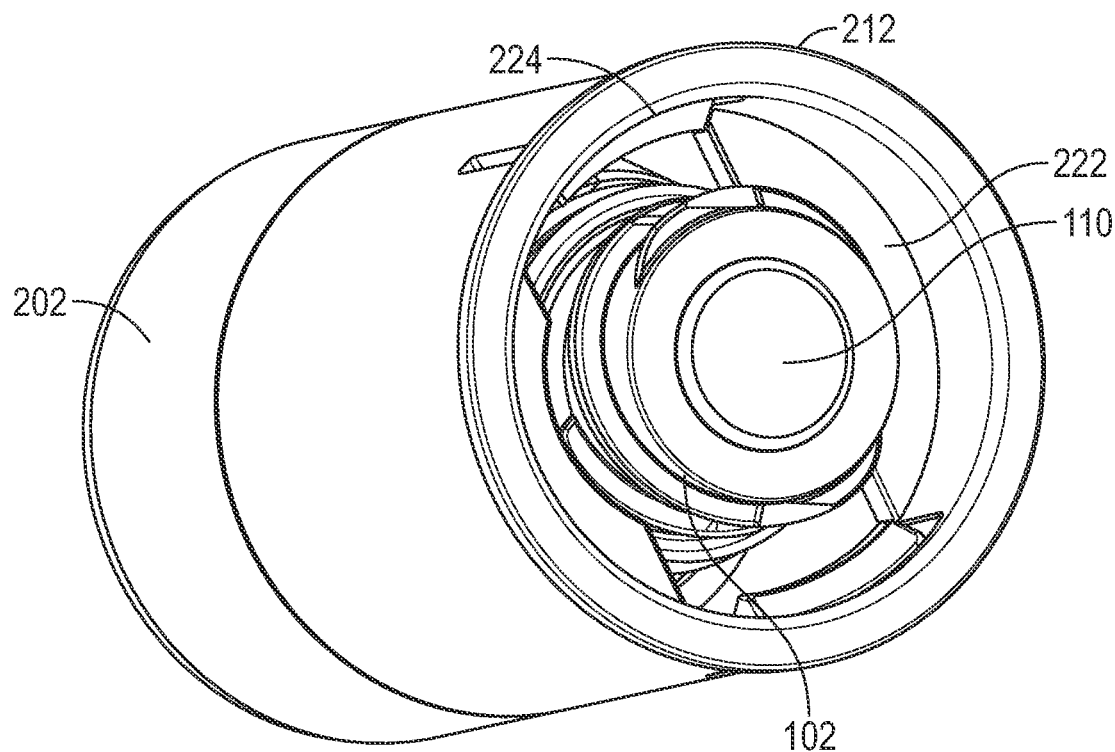
FIG. 9 illustrates a perspective view of a coupling mechanism coupled to the fluid connector assembly, in accordance with aspects of the present disclosure.

Referring to FIG. 7A, the first member 202 may include a first end 202A and a second end 202B opposite the first end. The second end 202B may include a first coupling portion 204 for coupling to the second member 212. In some embodiments, the first coupling portion 204 may be threaded. The first member 202 may include an interior surface 206 and an exterior surface 208. The first coupling portion 204 may be recessed relative the exterior surface 208 of the first member 202. In other words, the first member 202 may include a stepped profile along a longitudinal length of the first member 202 at the first coupling portion. The first member 202 may be generally hollow for housing at least a portion of the connector 102. The first member 202 may further include an opening 210 positioned at the first end 202A.

Referring to FIGS. 7B-9, the second member 212 may include a first end 212A and a second end 212B opposite the first end 212A. The second end 212B may include a second coupling portion 214 for coupling to the first coupling portion 204 of the first member 202. In some embodiments, the second coupling portion 214 may be threaded. The second member 212 may include an interior surface 216 and an exterior surface 218. The second coupling portion 214 may be recessed relative the interior surface 216 of the second member 212. In other words, the second member 212 may include a stepped profile along a longitudinal length of the interior surface 216 of the second member 212 at the second coupling portion. The second member 212 may be generally hollow for housing at least a portion of the connector 102. The second member 212 may further include an opening 220 at the second end 212B. The opening 220 may include one or more ribs, also referred to as an internal boss, 222 disposed on the interior surface 216 of along a perimeter of the opening 220 an extending inwardly toward a center of the opening 220.

In some embodiments, the second member 212 includes first and second ribs 222 disposed along opposing sides of the perimeter of the opening 220. The ribs 222 may include a concave profile. The second member 212 may further include one or more projections 224. The projections 224 may be disposed on the interior surface 216 proximate the second end 212B. The projections 224 may extend inwardly toward the center of the opening 220. In some embodiments, the second member 212 includes first and second projections 224 disposed on opposing sides of the second member 212. The second member 212 may include a plurality of slits 226 disposed adjacent the projections 224 and extending through the exterior surface 218. The slits 226 may allow the projections 224 to flex relative the exterior surface 218 of the second member 212.

Figure 6:
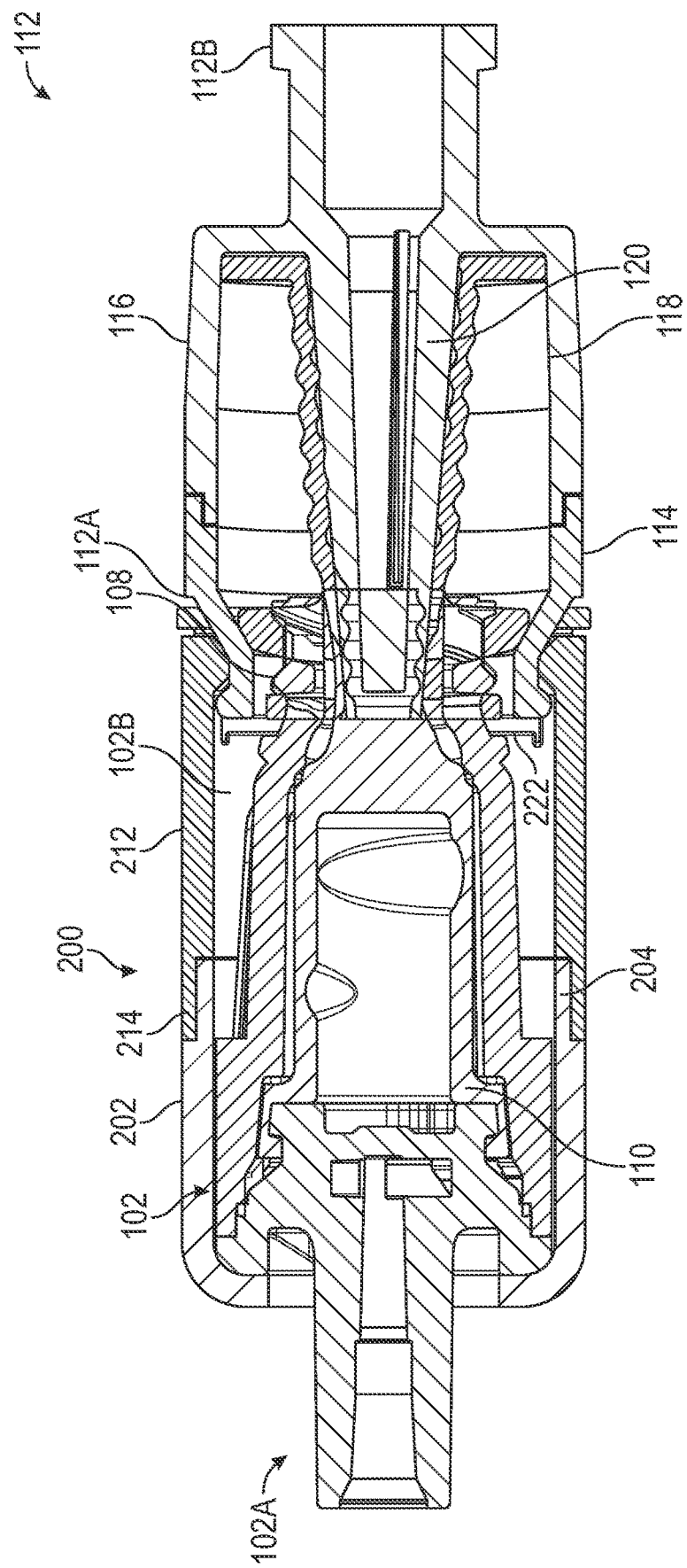
FIG. 6 illustrates a cross sectional view of the fluid connector and coupling mechanism of the fluid connector assembly, in accordance with aspects of the present disclosure.

Referring to FIG. 6, when the second member 212 is coupled to the connector 102, the ribs 222 may contact an exterior surface 104 of the connector 102. In particular, the concave profile of the ribs 222 may complement the threads 108 of the threaded portion of the connector 102. Moreover, when the second member 212 is coupled to the connector 102, the connector 102 may be substantially housed within the interior cavity of the second member, such that only a portion of the compressible member 110 extends past the second end 212B of the second member 212.

When the connector 112 is coupled to the connector 102, the first end 112A may be received within the opening 220 of the second member 212 such that an exterior surface 116 may contact ribs 222 and/or the projections 224. The positioning of the ribs 222 and the projections 224 may be such that an interstitial gap between the exterior surface 116 and the ribs 222 is limited thereby minimizing the chance of microbial growth.

The connectors 102, 112 may remain coupled until acted upon by a decoupling force. The decoupling force may pull first connector 102 away from second connector 112 or pull second connector 112 away from first connector 102. The decoupling force may act along an axis that is central to first connector 102 and second connector 112 while they are coupled. The decoupling force may be a resultant force acting along an axis central to first connector 102 and second connector 112 while they are coupled, or of a force that acts upon first connector 102 or upon second connector 112, or upon the first portion or tubing or upon the second portion of tubing.

The decoupling force may decouple first connector 102 from second connector 112 when decoupling force exceeds a predetermined threshold force. For example, if the decoupling force is less than the predetermined threshold force, the first connector 102 may not decouple from second connector 112. The predetermined threshold force prevents inadvertent or accidental decoupling based on minor forces or movements. When the connectors 102, 112 are decoupled, the coupling mechanism 200 may remain coupled to the connector 102.

In some embodiments, the predetermined threshold force is approximately 5 pounds (lbs). The predetermined threshold force may be from approximately 1 lb to approximately 8 lbs, approximately 3 lbs to approximately 7 lbs, approximately 4 lbs to approximately 6 lbs, or greater than 8 lbs.

Some embodiments herein related to methods for assembling the fluid connector assembly 100. For example, the connector 102 may first be positioned within an interior of first member 202 such that the first end 102A is positioned within and proximate the opening 210. The second member 212 may then be coupled to the first member 202 such that the first coupling portion 204 and couples to the second coupling portion 214. With the first member 202 and the second member 212 coupled to each other, the connector 102 may be substantially housed within the coupling mechanism 200. The connector 112 may then be coupled to the connector 102 such that the first end 112A of the connector 112 is positioned within or proximate the opening 220.

In some embodiments, the first member 202 and the second member 212 may be coupled to each other prior to positioning the connector 102 within the coupling mechanism 200.

The features of the present disclosure provide first and second compressible members that can be used as valves to regulate a fluid pathway therebetween. The first and second compressible members are located in a first and a second connector, respectively. If the first and second connectors are separated, whether unintentionally or intentionally, the fluid pathway for each of the first and second compressible members become closed or obstructed to prevent fluid loss therefrom. The features of the present disclosure also provide that upon separation of the first and second compressible members, any of the first and second compressible members can be cleaned and disinfected, and the first and second compressible members can be once again coupled together to form a fluid pathway therebetween.

Illustration of Subject Technology as Clauses

The subject technology is illustrated, for example, according to various aspects described below. Various examples of aspects of the subject technology are described as numbered clauses (1, 2, 3, etc.) for convenience. These are provided as examples and do not limit the subject technology. It is noted that any of the dependent clauses may be combined in any combination, and placed into a respective independent clause, e.g., clause 1, clause 9, or clause 15. The other clauses can be presented in a similar manner.

Clause 1. A coupling mechanism for a fluid connector assembly, the coupling mechanism comprising: a first member having a first end and a second end opposite the first end; and a second member comprising: a first end configured to detachably couple to the second end of the first member; and a second end opposite the first end, the second end having an opening and one or more ribs, wherein the one or more ribs are disposed along a perimeter of the opening and extend inwardly towards a center of the opening for engaging a portion of the fluid connector assembly, and wherein, when the coupling mechanism is coupled to the fluid connector assembly, an end of the fluid connector assembly extends beyond the second end of the second member.

Clause 2. The coupling mechanism described above, wherein first member further comprises a first coupling portion and the second member further comprises a second coupling portion, and wherein, when the first member and the second member are coupled, an exterior surface of the first coupling portion mates with an interior surface of the second coupling portion.

Clause 3. The coupling mechanism described above, wherein the first coupling portion and the second coupling portion are threaded.

Clause 4. The coupling mechanism described above, wherein the second member further comprises at least one projection disposed on an interior surface of the second member proximate the second end, and wherein the at least one projection extends inwardly toward the center of the opening of the second member and is configured to couple to a portion of the fluid connecting assembly.

Clause 5. The coupling mechanism described above, wherein the at least one projection is configured to flex with respect to other portions of the second member.

Clause 6. The coupling mechanism described above, wherein the at least one projection is disposed at a position closer to the second end of the second member than the one or more ribs.

Clause 7. The coupling mechanism described above, wherein the second member is configured to detach from the fluid connecting assembly upon a separating force exceeding a predetermined threshold.

Clause 8. The coupling mechanism described above, wherein the one or more ribs comprise a first rib disposed along a first side of the perimeter and a second rib disposed along a second side of the perimeter opposite the first side, and wherein each of the first rib and the second rib include a concave portion.

Clause 9. A fluid connector assembly comprising: a first connector; a second connector for coupling to the first connector; and a coupling mechanism configured to couple to the first connector, the coupling mechanism having: a first member having a first end and a second end opposite the first end; a second member having a first end configured to detachably couple to the second end of the first member and a second end opposite the first end and having at least one rib, wherein, when the coupling mechanism is coupled to the first connector, at least a portion of the first connector is disposed within an interior cavity formed by the coupling mechanism, and wherein, when the coupling mechanism is coupled to the first connector, the at least one rib contacts an exterior surface of the first connector.

Clause 10. The fluid connector assembly described above, wherein the second member further comprises at least one projection disposed at the second end, and wherein the at least one projection is configured to contact a portion of the second connector when the coupling mechanism is coupled to the first connector and the first connector is coupled to the second connector.

Clause 11. The fluid connector assembly described above, wherein the at least one projection is configured to flex with respect to another portion of the second member.

Clause 12. The fluid connector assembly described above, wherein first member further comprises a first coupling portion and the second member further comprises a second coupling portion, and wherein, when the first member and the second member are coupled, an exterior surface of the first coupling portion mates with an interior surface of the second coupling portion.

Clause 13. The coupling mechanism described above, wherein the first coupling portion and the second coupling portion are threaded.

Clause 14. The coupling mechanism described above, wherein the second member is configured to detach from the fluid connecting assembly upon a separating force exceeding a predetermined threshold.

Clause 15. A method for coupling a fluid connecting assembly, the method comprising:

providing a first connector having a first end and a second end opposite the first end and a second connector; providing a coupling mechanism having: a first member having a first end and a second end opposite the first end; a second member having a first end configured to detachably couple to the second end of the first member and a second end opposite the first end and having at least one rib; positioning the first end of the first connector within an interior of the first member of the coupling mechanism; detachably coupling the first member to the second member such that the first member is substantially disposed within an interior cavity of the coupling mechanism; and coupling the second connector to the first connector thereby forming a fluid pathway between the first connector and the second connector.

Clause 16. The method described above, wherein, detachably coupling the first member to the second member comprises coupling a first coupling portion of the first member and a second coupling portion of the second member via a threaded connection.

Clause 17. The method described above, wherein, when the first member is disposed within the interior cavity of the coupling mechanism, the at least one rib contacts an exterior surface of the first connector.

Clause 18. The method described above, wherein the second member further comprises at least one projection disposed on an interior surface of the second member proximate the second end, and wherein the at least one projection extends inwardly toward a center of an opening of the second member.

Clause 19. The method described above, wherein, when the second connector is coupled to the first connector, the at least one projection contacts an exterior surface of the second connector.

Clause 20. The method described above, wherein the second member is configured to detach from the fluid connecting assembly upon a separating force exceeding a predetermined threshold.

FURTHER CONSIDERATIONS

In some embodiments, any of the clauses herein may depend from any one of the independent clauses or any one of the dependent clauses. In one aspect, any of the clauses (e.g., dependent or independent clauses) may be combined with any other one or more clauses (e.g., dependent or independent clauses). In one aspect, a claim may include some or all of the words (e.g., steps, operations, means or components) recited in a clause, a sentence, a phrase or a paragraph. In one aspect, a claim may include some or all of the words recited in one or more clauses, sentences, phrases or paragraphs. In one aspect, some of the words in each of the clauses, sentences, phrases or paragraphs may be removed. In one aspect, additional words or elements may be added to a clause, a sentence, a phrase or a paragraph. In one aspect, the subject technology may be implemented without utilizing some of the components, elements, functions or operations described herein. In one aspect, the subject technology may be implemented utilizing additional components, elements, functions or operations.

The present disclosure is provided to enable any person skilled in the art to practice the various aspects described herein. The disclosure provides various examples of the subject technology, and the subject technology is not limited to these examples. Various modifications to these aspects will be readily apparent to those skilled in the art, and the generic principles defined herein may be applied to other aspects.

A reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the invention.

The word "exemplary" is used herein to mean "serving as an example or illustration." Any aspect or design described herein as "exemplary" is not necessarily to be construed as preferred or advantageous over other aspects or designs. In one aspect, various alternative configurations and operations described herein may be considered to be at least equivalent.

A phrase such as an "aspect" does not imply that such aspect is essential to the subject technology or that such aspect applies to all configurations of the subject technology. A disclosure relating to an aspect may apply to all configurations, or one or more configurations. An aspect may provide one or more examples. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples. A phrase such an embodiment may refer to one or more embodiments and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples. A phrase such a configuration may refer to one or more configurations and vice versa.

In one aspect, unless otherwise stated, all measurements, values, ratings, positions, magnitudes, sizes, and other specifications that are set forth in this specification, including in the claims that follow, are approximate, not exact. In one aspect, they are intended to have a reasonable range that is consistent with the functions to which they relate and with what is customary in the art to which they pertain.

In one aspect, the term "coupled" or the like may refer to being directly coupled. In another aspect, the term "coupled" or the like may refer to being indirectly coupled.

Terms such as "top," "bottom," "front," "rear" and the like if used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

Various items may be arranged differently (e.g., arranged in a different order, or partitioned in a different way) all without departing from the scope of the subject technology. All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112, sixth paragraph, unless the element is expressly recited using the phrase "means for" or, in the case of a method claim, the element is recited using the phrase "step for." Furthermore, to the extent that the term "include," "have," or the like is used, such term is intended to be inclusive in a manner similar to the term "comprise" as "comprise" is interpreted when employed as a transitional word in a claim.

The Title, Background, Summary, Brief Description of the Drawings and Abstract of the disclosure are hereby incorporated into the disclosure and are provided as illustrative examples of the disclosure, not as restrictive descriptions. It is submitted with the understanding that they will not be used to limit the scope or meaning of the claims. In addition, in the Detailed Description, it can be seen that the description provides illustrative examples and the various features are grouped together in various embodiments for the purpose of streamlining the disclosure. This method of disclosure is not to be interpreted as reflecting an intention that the claimed subject matter requires more features than are expressly recited in each claim. Rather, as the following claims reflect, inventive subject matter lies in less than all features of a single disclosed configuration or operation. The following claims are hereby incorporated into the Detailed Description, with each claim standing on its own as a separately claimed subject matter.

The claims are not intended to be limited to the aspects described herein but is to be accorded the full scope consistent with the language claims and to encompass all legal equivalents. Notwithstanding, none of the claims are intended to embrace subject matter that fails to satisfy the requirement of 35 U.S.C. § 101, 102, or 103, nor should they be interpreted in such a way.

What is claimed is:

1. A coupling mechanism for a fluid connector assembly having a first connector and a second connector, the coupling mechanism comprising:
   a first member having a first end and a second end opposite the first end; and
   a second member comprising:
      a first end configured to detachably couple to the second end of the first member; and
      a second end opposite the first end, the second end having an opening and one or more ribs and at least one projection configured to flex with respect to another portion of the second member,
   wherein the one or more ribs are disposed along a perimeter of the opening and extend inwardly towards a center of the opening for engaging a portion of the fluid connector assembly,
   wherein the at least one projection extends inwardly toward the center of the opening of the second member and is configured to couple to a portion of the second connector of the fluid connector assembly, and
   wherein, when the coupling mechanism is coupled to the fluid connector assembly, an end of the fluid connector assembly extends beyond the second end of the second member.

2. The coupling mechanism of claim 1, wherein first member further comprises a first coupling portion and the second member further comprises a second coupling portion, and
   wherein, when the first member and the second member are coupled, an exterior surface of the first coupling portion mates with an interior surface of the second coupling portion.

3. The coupling mechanism of claim 2, wherein the first coupling portion and the second coupling portion are threaded.

4. The coupling mechanism of claim 1, wherein the at least one projection is disposed at a position closer to the second end of the second member than the one or more ribs.

5. The coupling mechanism of claim 1, wherein the second member is configured to detach from the second connector of the fluid connector assembly upon a separating force exceeding a predetermined threshold.

6. The coupling mechanism of claim 1, wherein the one or more ribs comprise a first rib disposed along a first side of the perimeter and a second rib disposed along a second side of the perimeter opposite the first side, and wherein each of the first rib and the second rib include a concave portion.

7. A fluid connector assembly comprising:
   a first connector;
   a second connector for coupling to the first connector; and
   a coupling mechanism configured to couple to the first connector, the coupling mechanism having:
      a first member having a first end and a second end opposite the first end;

a second member having a first end configured to detachably couple to the second end of the first member and a second end opposite the first end and having at least one rib, wherein, when the coupling mechanism is coupled to the first connector, at least a portion of the first connector is disposed within an interior cavity formed by the coupling mechanism, and wherein, when the coupling mechanism is coupled to the first connector, the at least one rib contacts an exterior surface of the first connector.

8. The fluid connector assembly of claim 7, wherein the second member further comprises at least one projection disposed at the second end, and wherein the at least one projection is configured to contact a portion of the second connector when the coupling mechanism is coupled to the first connector and the first connector is coupled to the second connector.

9. The fluid connector assembly of claim 8, wherein the at least one projection is configured to flex with respect to another portion of the second member.

10. The fluid connector assembly of claim 7, wherein first member further comprises a first coupling portion and the second member further comprises a second coupling portion, and wherein, when the first member and the second member are coupled, an exterior surface of the first coupling portion mates with an interior surface of the second coupling portion.

11. The coupling mechanism of claim 10, wherein the first coupling portion and the second coupling portion are threaded.

12. The coupling mechanism of claim 7, wherein the second member is configured to detach from the second connector of the the fluid connector assembly upon a separating force exceeding a predetermined threshold.

13. A method for coupling a fluid connecting assembly, the method comprising:
providing a first connector having a first end and a second end opposite the first end and a second connector;
providing a coupling mechanism having:
a first member having a first end and a second end opposite the first end;
a second member having a first end configured to detachably couple to the second end of the first member and a second end opposite the first end and having at least one rib;
positioning the first end of the first connector within an interior of the first member of the coupling mechanism;
detachably coupling the first member to the second member such that the first connector is substantially disposed within an interior cavity of the coupling mechanism; and
coupling the second connector to the first connector thereby forming a fluid pathway between the first connector and the second connector.

14. The method of claim 13, wherein, detachably coupling the first member to the second member comprises coupling a first coupling portion of the first member and a second coupling portion of the second member via a threaded connection.

15. The method of claim 13, wherein, when the first connector is disposed within the interior cavity of the coupling mechanism, the at least one rib contacts an exterior surface of the first connector.

16. The method of claim 13, wherein the second member further comprises at least one projection disposed on an interior surface of the second member proximate the second end, and wherein the at least one projection extends inwardly toward a center of an opening of the second member.

17. The method of claim 16, wherein, when the second connector is coupled to the first connector, the at least one projection contacts an exterior surface of the second connector.

18. The method of claim 13, wherein the second member is configured to detach from the second connector of the fluid connecting assembly upon a separating force exceeding a predetermined threshold.

* * * * *